(12) United States Patent
Toledo Alonso et al.

(10) Patent No.: US 8,409,562 B2
(45) Date of Patent: Apr. 2, 2013

(54) CHIMERIC VACCINE ANTIGENS AGAINST CLASSICAL SWINE FEVER VIRUS

(75) Inventors: Jorge Roberto Toledo Alonso, Ciudad Habana (CU); Oliberto Sánchez Ramos, Ciudad Habana (CU); Maritza Isidra Barrera Valle, Ciudad de La Habana (CU); Nancy Elena Figueroa Baile, Ciudad Habana (CU); Yanet Prieto Carratala, La Habana (CU); Maria Pilar Rodriguez Molto, Cuidad de La Habana (CU); Maria Teresa Frias Lepoureau, Ciudad de La Habana (CU); Carlos Guillermo Borroto Nordelo, Ciudad Habana (CU)

(73) Assignees: Centro de Ingenieria Genetica y Biotecnologia, Ciudad de La Habana (CU); Centro Nacional de Sanidad Agropecuaria, La Habana (CU)

( * ) Notice: Subject to any disclaimer, the term of this patent is extended or adjusted under 35 U.S.C. 154(b) by 781 days.

(21) Appl. No.: 12/280,055

(22) PCT Filed: Feb. 28, 2007

(86) PCT No.: PCT/CU2007/000008
§ 371 (c)(1),
(2), (4) Date: May 18, 2009

(87) PCT Pub. No.: WO2007/098717
PCT Pub. Date: Sep. 7, 2007

(65) Prior Publication Data
US 2009/0304633 A1     Dec. 10, 2009

(30) Foreign Application Priority Data

Feb. 28, 2006   (CU) .................................. 2006-0052

(51) Int. Cl.
*A61K 38/21*     (2006.01)
*A61P 31/12*     (2006.01)
(52) U.S. Cl. ................... 424/85.7; 424/184.1; 424/85.1; 530/350; 435/69.7; 435/69.1; 435/5

(58) Field of Classification Search .................. None
See application file for complete search history.

(56) References Cited

FOREIGN PATENT DOCUMENTS

| EP | 1522585 | 4/2005 |
|---|---|---|
| EP | 1557084 | 7/2005 |

OTHER PUBLICATIONS

Accession No. Q5ZN69, Swiss-Prot, 2005.*
Accession No. Q95MQ5.2 Swiss-Prot, 2000.*
Wienhold, Daniel et al., "Immunomodulatory effect of plasmids co-expressing cytokines in classical swine fever virus subunit gp55/E2-DNA vaccination", Veterinary Research, Elsevier, Paris, NL, vol. 36, No. 4, Jul. 2005, pp. 571-587, XP002436548.
Huang, Hsing-I, "Improved Immunogenicity of a Self Tumor Antigen by Covalent Linkage to CD40 Ligand", International Journal of Cancer, New York, NY, US, vol. 108, 2004, pp. 696-703, XP002979404.
Van Rijn, P.A. et al., "An Experimental Marker Vaccine and Accompanying Serological Diagnostic Test Both Based on Envelope Glycoprotein E2 of Classical Swine Fever Virus (CSFV)", Vaccine, Butterworth Scientific, Guildford, GB, vol. 17, No. 5, Feb. 1999, pp. 433-440, XP004153825.
Armitage, R.J. et al., "CD40 Ligand is a T Cell Growth Factor", European Journal of Immunology, Weinheim, DE, vol. 23, Sep. 1, 1993, pp. 2326-2331, XP000573800.

* cited by examiner

*Primary Examiner* — Agnieszka Boesen
(74) *Attorney, Agent, or Firm* — Hoffmann & Baron, LLP (57) ABSTRACT

The current invention describes chimeric vaccine antigens against the virus that causes the Classic Swine Fever (CSFV). Such vaccine antigens are based on viral subunits coupled to proteins able to stimulate cellular and humoral immune system. Chimeric antigens can be produced in expression systems that guarantee a correct tertiary structure folding of the chimeric molecules, which constitute the essence of the current invention. The vaccine formulations containing such chimeric antigens induce an early and potent immune response on vaccinated pigs and confer full protection against CSFV. Moreover, the resultant vaccine formulations prevent the viral transmission from sows to their offspring. The chimeric antigens, as well as the resultant vaccine formulations, can be applied in animal health as vaccines for preventive use in swine.

8 Claims, 5 Drawing Sheets

CHIMERIC VACCINE ANTIGENS AGAINST CLASSICAL SWINE FEVER VIRUS

This application is the U.S. National Phase of, and Applicants claim priority from, International Application Number PCT/CU2007/000008 filed 28 Feb. 2007 and Cuban Application bearing Serial No. CU 2006-0052 filed 28 Feb. 2006, which are incorporated herein by reference.

TECHNICAL FIELD

The current invention is related to animal health, in particular with new chimeric antigens including viral subunits of Classic Swine Fever Virus (CSFV) coupled to proteins capable of stimulating cellular and humoral immune system, developing a potent and early immune response against such virus in pigs.

PREVIOUS ART

The Classic Swine Fever (CSF), also known as swine cholera for its highly infectious character and its worldwide distribution, it is considered the most important disease in pig and it is included in the notified diseases listing of the World Animal Health Organization. The etiological agent of this disease, CSFV, is a virus of the Pestvirus genus from the Flaviviridae family. It is known that it is a virus with a lipid envelope, diameter of 40 to 60 nm and hexagonal symmetry, with simple chain ribonucleic acid (RNA) as a genetic material (Kummerer et al. (2000). The genetic basis for cytopathogenicity of pestviruses. Vet. Microbiol. 77:117-128; Moenning et al. (2003). Clinical signs and epidemiology of Classical Swine Fever; a review of new Knowledge. Vet. Journal 165:11-20).

CSF is a highly contagious disease, in its acute form presents fever, degeneration of the capillary vessels, necrosis of the internal organs and death. The first clinical signs appears after an incubation period from 2 to 6 days, producing pirexia, reduction of movements and anorexia, getting worse in the following days and the body temperature can reach 42° C. Also, a leukopenia is developed, with values of white series smaller than $8000/mm^3$ of blood. The pigs also develop conjunctivitis, constipation followed by diarrhea, vomiting, lack of movement coordination, convulsion and muscular paresis in the terminal phase. It is evident a red skin color diffused through the whole abdomen, snout, ears and the internal part of the legs. In most of the fatal cases the histopathology of brain shows a non suppurative encephalitis with high vascularization (Moenning et al. (2002) Clinical Signs and Epidemiology of Classical Swine Fever. A review of new knowledge. Vet. Journal 161:1-10).

The CSFV acts like an immunosuppressor during the infection (Susa et. Al. (1992) Pathogenesis of Classical Swine Fever: B-lymphocyte deficiency caused by Hog Cholera virus. J. Virol. 66:1171-1175) and the detection of neutralizing antibodies begins on weeks 2 and 3 after the infection (Laevens et. Al. (1998). An experimental infection with a classical swine fever virus in weaner pigs. II. The use of serological data to estimate the day of virus introduction in natural outbreaks. Vet. Q. 20: 46-49). The terminal stage of the infection is associated with a remarkable decrease of lymphocytes B on the circulatory system, as well as on lymphoid tissue (Susa et al. (1992). Pathogenesis of Classical Swine Fever: B-lymphocyte deficiency caused hog cholera virus. J. Virol. 66: 1171-1175). Most of the pigs which get the disease died between days 10 and 20 subsequent to the infection, with mortality over to 95%. The post mortem lesions characteristic to CSF belong to a hemorrhagic diathesis with petechiae in the majority of the organs systems. These are more regular on kidneys, urinary bladder and lymphatic ganglia, although, they can appear also, in spleen, larynx, mucosa and serosa (Mouwen et al. (1983) Atlas of Veterinary Pathology, Bunge, Utrecht The Netherlands).

The transplacental infection is other clinical form of the CSF; in this case the virus is capable to pass through the pregnant sows placenta infecting the fetuses. The consequences of this infection can be abortion, birth of dead offspring, mummifications, malformations, birth of weak pigs and problems in organs differentiation. Depending on the gestation time in which infection occurs, CSFV immune-tolerant offspring can be born as a result of infection through the sows (vertical transmission). Piglets remain infected and viremics until death, generating a stable CSFV dissemination focus on the herd (Moenning et al, (2003) Clinical Signs and Epidemiology of Classical Swine Fever: a review of new knowledge. Vet. Journal 165:11-20). Mortality associated to CSF constitutes an economic problem for the affected countries, having influence on the damage of the economic and social situation of developing nations. For these reasons, in countries with a high swine density and high prevalence of the virus, it becomes necessary to apply control programs based on vaccination. In highly developed countries in which swine production is mainly subsidized by the governments, as Europe, United States and Canada, it is applied the eradication method by stamping-out. However, costs are very high and those countries are still susceptible to possible epizooties.

The European Union (EU) is considered a high risk zone of re-emergence of new CSFV epizooties due to the high density of the swine population, to the non vaccination policy and to its geographical proximity with the Eastern European countries, where the CSFV is enzootic. One of the problems associated with the emergence of new epizooties in this region is the presence of wild boars with endemic infections of CSF (Laddomada (2000) Incidence and control of CSF in wild boars in Europe. Vet. Microb, 73:(121-30). These apparition of new epizooties have occurred in spite of the solid programs of control that are implemented inside the European Union, which include the sanitary sacrifice of the whole contagious population and the restriction of swine exportation from affected zones to disease-free zones (van Oirschot (2003) Vaccinology of Classical Swine Fever: from lab to field. Vet Microbiol, 96:367-384). Then, it is urgent the necessity of developing vaccines that induce an immune response, early and secure, which guarantee the protection against the infection and the viral transmission.

Vaccines against CSFV based on virus intact have been developed: vaccines with crystal violet or formalin-inactivated virus (Biront et al. (1988) Classical swine fever related infections. Liess B. M. Ed. Martinus Nijhoff Publishing, Boston: 181-200), vaccines with virus attenuated through passages in rabbit, like Sinlak strain (Baibikov et al. RU 2182495) and the Lapinizied Chinese strain (Dahle et. Al (1995) Assessment of safety and protective value of a cell culture modified strain C vaccine of hog cholera/classical swine fever virus. Berl-Munch. Tieraztl.Wsch, 108:20-25), or vaccines with virus attenuated in tissue cultures coming from rabbit, guinea pig, and pig (Kachiku et al. JP 73001484; Terpstra et al. (1990) Development and properties of a cell culture produced for hog cholera based on Chinese strain. Ditsh. Tierarztl.Wsch. 97: 77-79) These types of vaccines constitute a risk due to the possibility of containing fractions of active virus that, inoculated on susceptible animals will produce new CSF outbreaks. Besides, in some cases repetitive immunizations are needed to obtain the protective immunological response because the inactivation affects the immunogenic properties of the virus.

In the specific case of live vaccines with attenuated virulence, they have the potential risk that a partial attenuation or virulence reversion occurs. In any of the cases they will produce pathogenic viral particles, that inoculated on susceptible animals, allow the infection, the clinical disease and the spreading of CSF on the herds. These problems bring about a bigger risk for pregnant sows because the virus can infect the fetuses, which are highly susceptible and infected offspring spread the disease. There are vaccines based on CSFV strains that have demonstrated to be attenuated, like the C Chinese strain, PAV 250 strain, Thierval strain and the IFFA/A-49 strain (Björlund, H. J V. et. Al (1998) Molecular characterization of the 3' noncoding region of classical swine fever virus vaccine strains. Virus Genes 16: 307-312, Launais et al. (1978) Hog Cholera Virus: Active immunization of piglets with the Thiverval strain in the presence and absence of calostral passive immunity. Vet. Microbiology 3:31-43). These strains are only used in countries where the disease is enzootic, because they have as inconvenient that they do not allow the differentiation between a vaccinated animal and the one infected with the native virus. Animals vaccinated with these strains produce identical responses in the serological tests, like in the infected animals. The specific antibodies anti-CSFV which are generated with the vaccines based on attenuated virus interfere with the diagnostic of the infection by CSF. The diagnostic is carry out by the immune-detection of the infective virus in tonsils and the multiplication of vaccine viral strain occur in tonsils. For these reasons, the attenuated strains are not suitable to be used in the eradication programs. The vaccination with LK-VNIIVVM strain and additional hyper-immunization with the purified strain Shi-Myng, formulated with Freund's adjuvant is another example. But, the immunization in 40-45 places is not feasible on a vaccination campaign where hundred of animals must be vaccinated daily (Balashova et al. RU2183972).

Immunization with these vaccines, containing the whole virus, interfere also with the differential diagnostic among infections caused by the CSFV and the ones caused by other members of the Pestvirus genus that can infect pigs, like Bovine Viral Diarrhea Virus (abbreviated BVDV) and the Border Disease Virus (abbreviated, BDV), (Dahle et al. (1991) Clinical Post Mortem and Virological Findings after Simultaneous Inoculation of Pigs with Hog Cholera and BVD Virus. J. Med. Vet. 38: 764-772).

To avoid the inconveniences of the vaccines based on whole virus, results suitable to use vaccines totally innocuous, as the variants based on subunits, or in viral protein obtained by recombinant way. These variants should protect herds from the reintroduction of viral strains and also, to allow the differentiation between the vaccinated and infected animals by simple serological methods. In this sense, vaccines based on viral subunits have been developed. Vaccines containing viral proteins like E2 glycoprotein of viral envelope (Bourna et al. (2000) Duration of the onset of the herd immunity induced by E2 subunit vaccine against classical Swine Fever virus. Vaccine 18: 1374-1381) are safe, because their use do not involve any risk of reversion to the virulence and do not interfere with the diagnostic. These vaccines allow differentiating between the infected animals and the vaccinated ones, because the antibodies that are generated are reactive only against a viral segment. Then, they are convenient for a CSF eradication program.

Several recombinant vaccines that express E2 protein on prokaryotes and vaccines based on synthetic peptides of such protein have been developed (Chen et al. WO 200232453). In these cases the protein is not glycosylated, so its immunogenicity and protective capacity are affected. Another vaccine candidates use viral vectors for the expression of the heterologous gene of E2 in eukaryote cells like the swine pseudorabies virus (Peeters et al. (1997). Biologically safe, non-transmissible pseudorabies virus vector vaccine protects pigs against both Aujeszky's disease and classical swine fever. J. Gen. Virol. 78: 3311-3315), the smallpox swine virus (Gibbs et al. U.S. Pat. No. 62,117,882) and the swine adenovirus (Nagy et al. WO200183737). In these cases, the viral infection with wild type virus produces neutralizing antibodies against the viral vector of same serotype. Thus, the induction of the immune response against CSFV is affected. Also, viral vectors based on the swine pseudorabies virus and in the swine smallpox virus can not be applied in countries declared free from these viruses, due to regulatory problems. Also, vaccinia virus has been used as a vector but regulations from the World Health Organization hinder its use (Meyeers et al. EP 1087014).

Vaccines based on naked desoxirribonucleic acid (DNA) for the expression of the E2 protein in myocite and osteocyte have the inconvenience that higher concentrations of DNA are required to induce a response, because the transfection with naked DNA is very inefficient. This vaccine is submitted to strong regulatory controls that hinder its application (Audonnet et al. WO 20152888).

The production of E2-CSFV as antigen in the insect cells expression system mediated by Baculovirus has resulted a feasible alternative (Van-Rjin et al. (1999). An experimental marker vaccine and accompanying serological diagnostic test both based on enveloped glycoprotein E2 of classical swine fever virus. Vaccine, 17: 433-440; Kretzdorn et al. U.S. Pat. No. 20040028701). In this system the recombinant E2 is produced as a glycoprotein, increasing its immunogenicity respect to the non glycosylated isoform. The bacoluvirus is further inactivated and there are no pathogenic effects for the pigs. However, the effective protection against the infection is induced after three weeks post-vaccination and there is not a complete protection against the intrauterine infection. Therefore, an important problem in CSF prevention is that there are no subunit recombinant vaccines allowing a differential diagnostic among vaccinated and infected animals and being capable of producing an early protection after vaccination abolishing the transplacental transmission of pregnant sows to their offspring.

DESCRIPTION OF THE INVENTION

The current invention solves the problem mentioned before. The new vaccine contains chimeric antigens comprising viral subunits combined to immune system-stimulating molecules, which allow the development of an early immune response that protects pigs from the CSFV infection. Another advantage of the solution proposed is that it abolishes the viral transmission from the infected pregnant sows to its offspring, due to the immuno-enhancement effect of stimulating molecules that are combined with the viral proteins in the chimeric antigens.

Particularly, the invention refers to chimeric antigens against CSF which have as main component the E2 glycoprotein from the CSFV envelope. The extracellular segment of E2 glycoprotein is used as immunogen coupled to an immune system-stimulating protein (named in the context of this invention "molecular adjuvant"), to enhance both the stimulation of an early cellular immune response and the induction of higher CSFV neutralizing antibodies titers.

In a particular embodiment of the invention, the immune system-stimulating protein is the alpha interferon or the extracellular segment of the CD154 molecule. On a preferred embodiment, alpha interferon or the extracellular segment of CD154 molecule could come from any mammal.

The vaccine antigens of the present invention, based on chimeric proteins, guarantee a protection on vaccinated pigs since the first week after the immunization, when they are challenged with $10^5$ $DL_{50}$ (Dose of the virus which cause the death of 50% of the CSFV infected animals). Such protection is mediated by a strong cellular immune response against CSFV, which is directly related with the combination of elements that are combined in the chimeric antigen. It is also observed, a time reduction in the neutralizing antibodies induction, which appear in the second week subsequent to vaccination. This contributes to increase the protection against CSFV on vaccinated pigs. Immunized animals do not present evidences of the clinical disease, and the CSFV could not be isolated from the corporal fluids in any day after the challenge with such virus.

E2-molecular adjuvant chimeric antigens prevent the vertical transmission of CSFV from the sows to their fetuses. These proteins induce an early protection in pregnant sows, which delay the development of the clinical disease and do not allow the virus multiplication, not only in mothers but also in the fetuses, after the challenge with $10^5$ $DL_{50}$ of CSFV.

In a preferred embodiment, the chimeric vaccine antigen is characterized for containing essentially the amino acid sequence of the extracellular segment (or domain) of the E2 glycoprotein of CSFV, which appears on the Sequence Listing as Seq ID. No. 1; and the extracellular segment of CD154 molecule from pig as Seq ID. 2. The chimeric vaccine antigen essentially comprises such amino acid sequences, but it can also include the extracellular segment of E2 from any isolate of CSFV. Another aspect from the current invention is that the chimeric vaccine antigens can be obtained by recombinant, synthetic way or by chemical conjugation. In a particular embodiment of the invention, a variant based on a chimeric protein containing E2his (the extracellular segment of E2 fused to a tail of 6 histidines) and a molecular adjuvant was generated as a fusion protein. With this purpose, a spacer peptide consisting of 4 repeated units of $Gly_4Ser$ ($4G_4S$) and a stimulating molecule of the immune system was added to the C-terminal extreme of E2his. The incorporation of the $4G_4S$ peptide allows a certain degree of relaxation to the polypeptide chain. This guarantees the correct tertiary structure folding of the protein structure to obtain the proteins fused with a tertiary structure, similar to the native one. One of the vaccine antigens, object of this invention, has the extracellular domain of the swine CD154 molecule fused in its C-terminal end, as molecular adjuvant (E2his-CD154).

Up to now, the production of recombinant vaccine candidates against CSFV mediated by the expression systems in animals as bioreactors has not been explored. Nevertheless, the capacity of the mammary gland to express glycosylated recombinant proteins with a correct folding of its tertiary structure, constitute an adequate expression system to produce the E2 glycoprotein with high immunogenicity and protective capacity. Transient expression system in the mammary gland of ruminant, mediated by adenoviral vectors, constitutes a tool to obtain high expression levels of recombinant proteins in a fast and simple way (Toledo et al., WO 2004/034780). This method results very useful for the production of E2 recombinant with the purpose of applying vaccination programs directed to the eradication of CSF. In a materialization of the invention, the vaccine antigens object of this invention are expressed in the mammary epithelial cells of genetically modified mammalians, during the lactation process and are secreted in the milk. The recombinant chimeric molecules are produced in the milk of the transgenic mammalians or by the direct transformation of the mammary glandular epithelium of non transgenic mammalians, with the employment of adenoviral vectors. In other materialization of the invention, the chimeric vaccine antigens are produced in genetically modified yeasts. Such antigens are obtained in the culture medium of the yeast transformed with the chimeric gene and the regulatory sequences allowing the expression and secretion of the recombinant protein to the culture medium.

E2 protein of native CSFV is exposed as a homodimer on the viral envelope, stabilized by inter-chain disulphide bridges. This determines that neutralizing and protective antibodies are generated against conformational epitopes present on the homodimers. The vaccine antigens developed during the current invention are produced in expression systems which allow the correct folding of these recombinant proteins. The design of genetic constructs guarantees no alteration of the tertiary structure of the fusions proteins. Recombinant vaccine antigens are easily purified by a simple chromatographic step of affinity to metallic ions.

The design of genetic constructs, the usage of expression systems and the relative simplicity of the purification procedure guarantees that the vaccine antigens against CSFV, described on the current invention, keep the antigenic and immunogenic properties similar to viral E2 protein. The immunization with chimeric molecules, produced in expression systems as *Pichia pastoris* or the goat's mammary gland, leads to a potent and early immune response. The extracellular domain of E2 generates homodimers that provide the conformational epitopes for the generation of the neutralizing and protective antibodies. The segment from CD154 acts as a molecular adjuvant, which stimulates the immune system of the vaccinated pigs, produces a cellular immune response that protects animals from CSFV, since the first week subsequent to vaccination. The combination of both molecules in the chimeric protein, that contains a spacer peptide, guarantees the correct folding of each molecule. The expression systems used allow that the recombinant proteins being expressed in its glycosylated isoform. It also helps to obtain the molecules with the proper tertiary structure.

Another aspect of the present invention are the vaccine formulations with the capability for producing a protective immune response against CSFV, which are characterized for comprising the chimeric antigens described before containing the extracellular domain of E2 glycoprotein and a molecular adjuvant. Such vaccine formulations can be administered to animals by a systemic or mucosal route, with the purpose of preventing CSF, and avoiding the material and economic losses that are produced by CSFV infection in the swine herds.

BRIEF DESCRIPTION OF THE DRAWINGS

FIG. 5. Purity and identification analysis of E2his separated in SDS-PAGE in non reducing conditions. The protein was expressed in the milk of goats transduced with Ad-E2his-sec vector and the purification was carried out by ion metal affinity chromatography. (A) SDS-PAGE of the different steps of purification. (B) Immune-identification by Western blotting using Mab 1G6. Lane 1: positive control of E2his expressed in the culture medium of PK-15 cells transduced with Ad-E2his-sec vector, Lane 2: milk serum samples from untreated goats, Lane 3: milk serum samples from goats transduced with the Ad-E2his-sec vector, taken as initial material for the chromatography, Lane 4: material not bound to the matrix, Lane 5: washing with 20 mM imidazole, Lane 6: washing with 50 mM imidazole, Lane 7: elution at 200 mM imidazol.

INCORPORATION OF SEQUENCE LISTING

Incorporated herein by reference in its entirety is the Sequence Listing for the application. The Sequence Listing is disclosed on a computer-readable ASCII text file titled, "sequence.txt", created on May 14, 2009. The sequence.txt file is 6 kb in size.

EXAMPLES

Example 1

Amplification of the Gene Segments Coding for the Extracellular Domains of the CSFV E2 and Swine CD154, and Cloning of the pMOS-E2his-CD154 Plasmid The gene segment coding for the extracellular domain of E2, of 363 amino acid, was amplified by reverse transcription and polymerase chain reaction (RT-PCR), from the viral genome of the Cuban CSFV isolation "Margarita" strain, access number AJ704817 on the data base of the National Center for Biotechnology Information (NCBI). In the 3' oligo was included the coding sequence for a tail of 6 histidines, in order to allow an easy purification of the antigen.

The coding sequence for the extracellular domain of swine CD154, of 210 amino acids was obtained by chemical synthesis taking the CD154 gene of pig *Sus scrofa* (NBCI access number AB040443) like sequence pattern. In the 5' end of the coding sequence for such molecule was included a region coding for a peptide of four repeated units of Gly-Gly-Gly-Gly-Ser ($4G_4S$). Through a subcloning in the pMOS-BLUE plasmid (Amersham, USA) the synthesized sequence ($4G_4S$-CD154) was inserted just after the tail of 6 histidines in the coding sequence of E2his. pMOS-E2his-CD154 plasmid was obtained.

Example 2

Genetic Constructions of E2his and E2his-CD154 Molecules with Secretion Signals for Mammalian Cells The sequence corresponding to E2his, obtained by RT-PCR was inserted in the Bgl II-EcoR V sites of plasmid pAEC-SPT (Herrera et al. (2000) Biochem. Byophys Res. Commun. 279:548-551). Thus, the vector pE2his-sec was obtained containing the coding sequence for E2his preceded by the secretion signal of the human tissue plasminogen activator (htPA) and under the transcriptional control of the early immediate promoter of human cytomegalovirus (CMVP).

The sequence corresponding to E2his-CD154, subcloned in the pMOS-BLUE vector, was inserted in the restriction sites for endonucleases Bgl II-Sal I in the plasmid pAEC-STP. Thus, it was obtained the vector pE2hisCD154-sec containing the coding sequence for E2his-CD154, preceded by secretion signal of htPA and under the transcriptional control of PMCV.

Example 3

Generation of Recombinant Adenoviral Vectors Containing the Coding Sequences for E2his and E2his-CD154 with Secretion Signals for Mammalian Cells Adenoviral vectors with defective replication (Ad-ΔE1, ΔE3) were generated as described the AdEasy system guide (AdEasy™-Vector system, Quantum Biotechnologies, EE.UU). The plasmid pAdTrack-CMV was used as transfer vector. The coding sequence for E2his, with the signal secretion of htPA (E2his-sec), was extracted from the plasmid pE2his-sec by enzymatic digestion with the Nco I and EcoR V restriction endonucleases and it was inserted in the EcoR V restriction site of the pAdTrack vector. The recombinant pAdT-E2his-sec with the secretable variant of E2his under the transcriptional control of the PCMV was obtained.

The coding sequence for secretable E2his-CD154 was extracted from the plasmid pE2his-CD154-sec by enzymatic digestion with the Nco I and Sal I restriction endonucleases and it was inserted in the Kpn I-Xho I restriction sites of the pAdTrack vector. The recombinant pAdT-E2hisCD154-sec with the E2his-CD154sec under the transcriptional control of the PCMV was obtained.

The transfer adenoviral vectors, pAdT-E2his-sec and pAdT-E2hisCd154-sec, were linealized by enzymatic digestion with the Pme I restriction endonuclease in order to generate the recombinant adenoviral genomes. Each of the linear vectors was separately co-electroporated with pAdEASY-1 vector in the *Escherichia coli* BJ5183 strain. The recombinant genomes of both pAd-E2his-sec and the pAd-E2hisCD154-sec vectors were obtained by recombination of homologues. One of them contains the coding sequence for E2his-sec and the other one the coding sequence for the molecule of E2his-CD154-sec. In both cases they remained under the transcriptional control of the PCMV.

Figure 1:
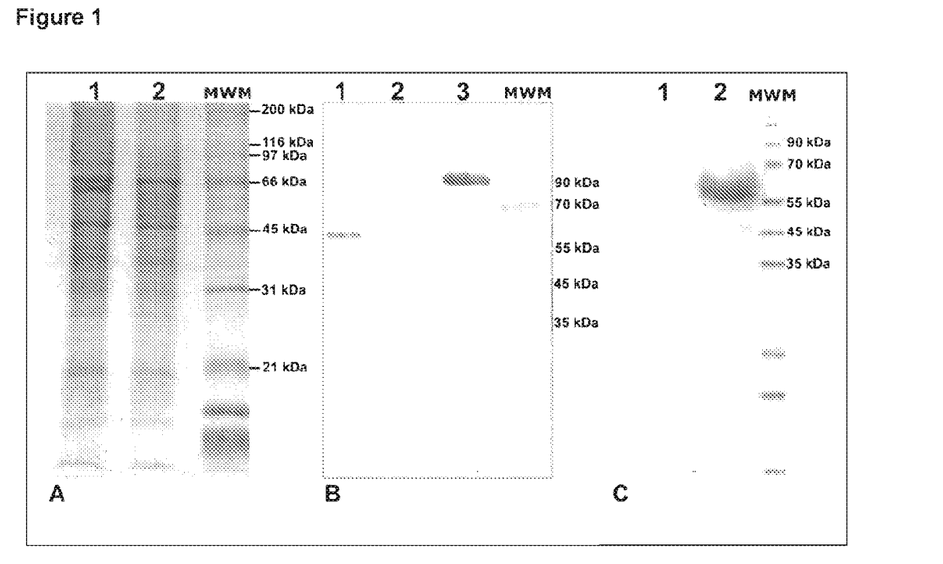
FIG. 1. Analysis by SDS-PAGE, in reducing conditions, of the E2his expression in PK-15 cells transduced with the Ad-E2his-sec adenoviral vectors. (A) SDS-PAGE, lane 1: culture medium from transduced cells, Lane 2: culture medium from untreated cells, MWM: molecular weight marker. (B) Immune-identification of E2his by Western-blotting using a monoclonal antibody directed against the histidine tail, Lane 1: culture medium from transduced cells, Lane 2: culture medium from untreated cells, Lane 3: positive control for histidine tail, MWM: molecular weight marker. (C) immune-identification of E2his by Western blotting using a polyclonal serum from CSFV infected pigs, lane 1: culture medium from untreated cells, Lane 2: culture medium from cells transduced with Ad-E2his, MWM: molecular weight marker.
Figure 2:
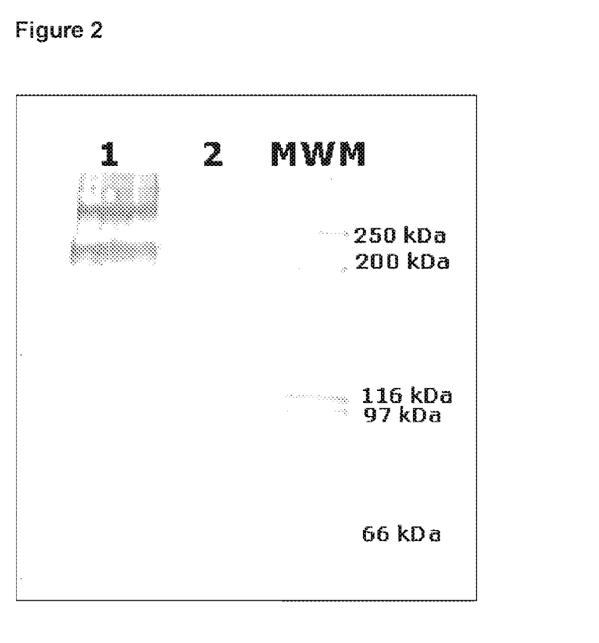
FIG. 2. Analysis of the E2his expression conditions and the E2his-CD154 in PK-15 cells transduced with Ad-E2his-sec and Ad-E2hisCD154-sec adenoviral vectors. The proteins in the culture medium were separated by SDS-PAGE in non reducing conditions. The immuno-identification of molecules of interest was carried out by Western blotting using a monoclonal antibody (Mab) against E2 protein of CSFV (Mab-1G6). Lane 1: culture medium from cells transduced with Ad-E2his-sec vector, Lane 2: culture medium from cells transduced with Ad-E2hisCd154-sec vector, MWM: molecular weight marker.
Figure 3:
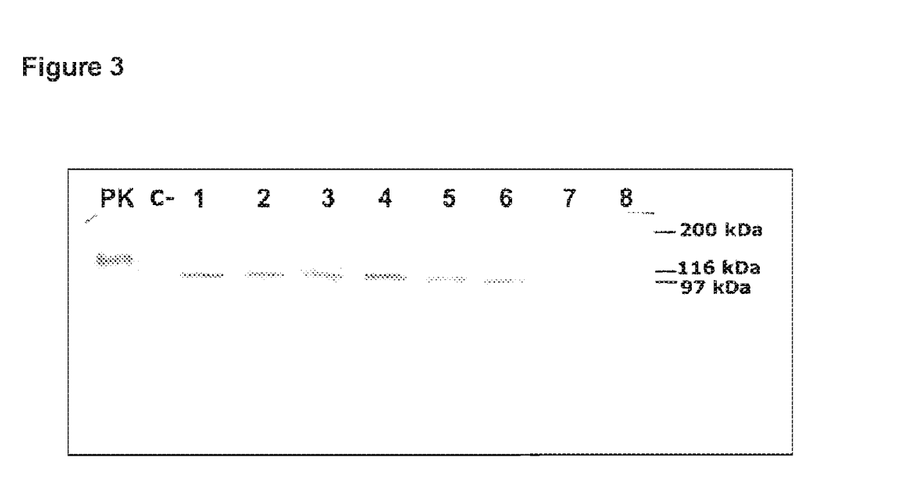
FIG. 3. Kinetics of the expression of E2his in the milk of goats transduced with Ad-E2his-sec vector. The proteins from milk serum samples corresponding to each day of milking were separated by SDS-PAGE in non reducing conditions. The immune-identification of E2his was assayed by Western blotting using the Mab-1G6. Lane PK: positive control of E2his expressed in the culture medium of PK-15 cells transduced with Ad-E2his-sec vector, lane C-: milk serum samples from untreated goats, Lanes 1-8: milk serum samples from goats transduced with Ad-E2his-sec vector, corresponding to each of the 8 days of milking subsequent to the adenoviral transduction.
Figure 4:
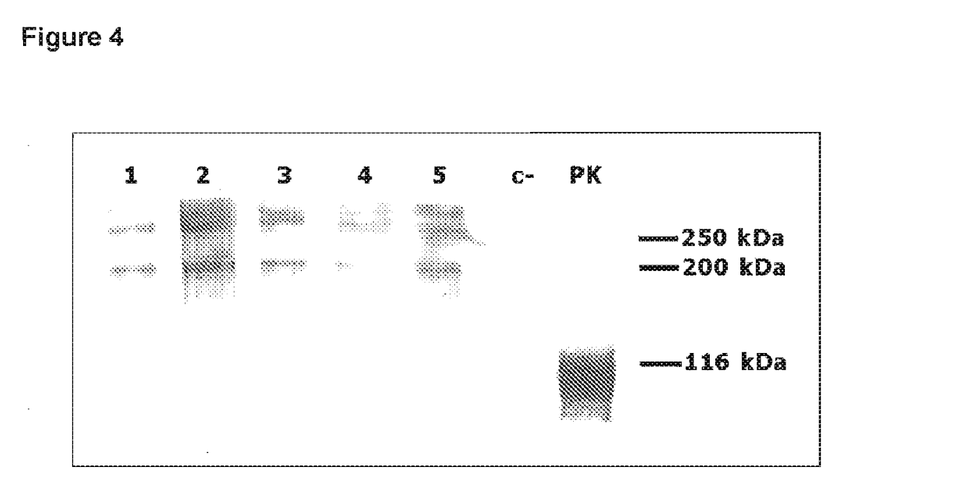
FIG. 4. Kinetics of expression of E2his-CD154 in the milk of goats transduced with Ad-E2hisCd154-sec. The proteins present in the milk serum samples corresponding to each day of milking were separated by SDS-PAGE in non reducing conditions. The immune-identification of E2his-CD154 molecule was carried out by Western blotting using the Mab-1G6. Lanes 1-5: milk serum samples from goats transduced with the Ad-E2hisCD154-sec vector corresponding to each of the 5 milking days subsequent to the adenoviral transduction, Lane C-: milk serum samples from untreated goats, Lane PK: positive control of E2his-CD154 expressed in the culture medium of PK-15 cells transduced with Ad-E2hisCD154-sec vector.
Figure 5:
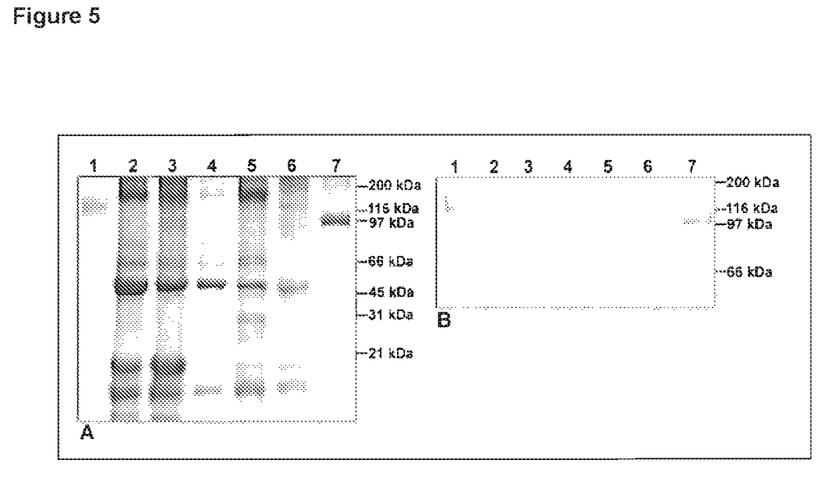
Figure 6:
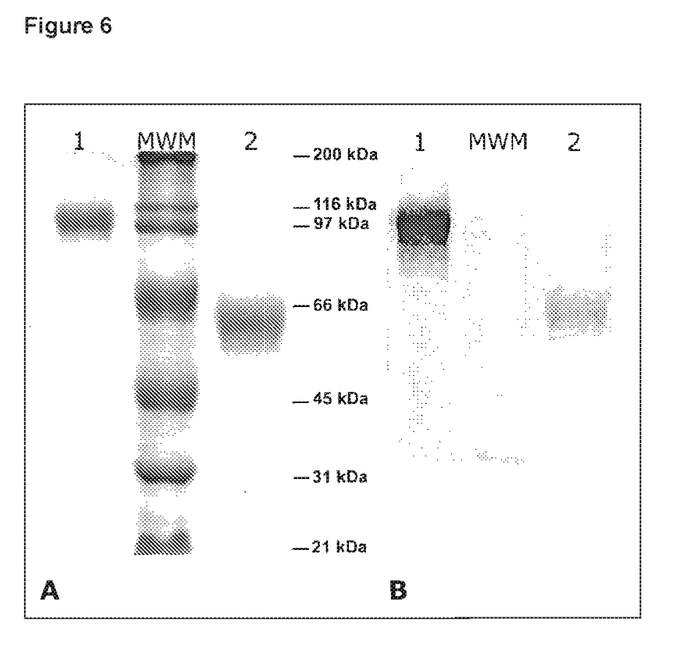
FIG. 6. Comparison of the antigenic recognition of two isoforms of the E2his vaccine antigen by antibodies present in the serum of pigs infected with a virulent strain of CSFV. E2his purified from the milk of goats transformed with the Ad-E2his-sec adenovirus vector was analyzed by electrophoresis and Western blotting assay in reducing conditions (monomer) and non reducing conditions (homodimer). (A) SDS-PAGE. (B) Western blotting using a polyclonal serum of CSF infected pigs, Lane 1: E2his separated in non reducing conditions, Lane 2: E2 his separated in reducing conditions.

Recombinant adenoviral genomes were further digested with the Pac I endonuclease and transfected separately in the HEK-293A complementary cells line and the infective virion were obtained. Two adenoviral vectors were generated: Ad-E2his-sec and Ad-E2hisCD154-sec. The vectors were amplified independently in the HEK-293A cell line, until titers of $1\times10^{12}$ colony forming units/mL (CFU/mL) were obtained and it were purified by a double centrifugation in CsCl gradient. The vectors were further dialyzed against storage buffer (10 mM Tris pH 8.0, 2 mM $MgCl_2$, 4% sacarose) and were kept at $-70°$ C. The capacity of Ad-E2his-sec and Ad-E2hisCD154-sec adenoviral vectors to transform mammalian cells and to mediate the expression and secretion of molecules of E2his and E2his-CD154 to the culture medium were corroborated by infection assays in the PK15 pig cell line. The protein samples present in the culture medium of the infected cells were separated by sodium dodecyl sulphate-polyacrylamide gel electrophoresis (SDS-PAGE), in non reducing conditions and were analyzed by Western blotting assay with a monoclonal antibody against E2 of CSFV (αE2-1G6) (FIGS. 1 and 2).

The analysis of the molecular weight of E2his and E2his-CD154 glycoproteins proved that they corresponded with dimeric and trimeric isoforms. In lane 1, FIG. 2, two bands corresponding to dimeric (180 kDa) and the trimeric isoforms of E2-CD154 (270 kDa) are observed.

Example 4

In Situ Transduction of Goat Mammary Glandular Epithelium for the Production of E2his and E2his-CD154 in the Milk For the mammary epithelium transformation with the expression cassettes E2his and E2his-CD154, the Ad-E2his-sec and Ad-E2hisCD154-sec recombinant adenoviral vectors were used. In both cases, the vectors were inoculated in the mammary gland of lactating goats by the direct infusion of the udder through the nipple's channel. Adenoviral vectors infected the secretory epithelial cells that conforms the mammary epithelium allowing the expression of the recombinant proteins.

Goats in the second month of natural lactation, with a production average of 1 liter per day were employed. The females were initially milked until removing the milk from the udders in order to transduce the adenoviral vectors, subsequently isosmotic saline solution was infused to the cisterns directly through the nipples' channel, making soft massages of the udder to guarantee the total washing of the mammary gland. Saline solution was removed by an exhaustive milking of the udder and the process was repeated twice. Subsequently, the adenoviral inoculum was infused with a titer of $10^9$ CFU/mL in saline solution, containing 36 mM of EGTA. The infusion volume for each udder was variable and was guaranteed the total filling of the cisterns, depending of the capacity of the udder. After the infusion were applied udder massages in order to facilitate a homogeneous distribution of adenoviral inoculums in way in the gland reaching until the secretor epithelial cells of the alveoli. The adenoviral inoculums were removed 24 hours after by milking. With the aim of eliminate the remnant adenoviral vectors on the cistern or in the mammary ducts, the mammary glands were flushed again through the infusion of saline solution.

Twenty four hours later the collection of milk from the transformed animals began, by manual milking. Two daily milking were performed with 12 hours intervals. The collected milk was stored at −70° C. The expression kinetics of E2his and E2his-CD154 recombinant proteins in the milk was analyzed for each milking samples (FIGS. 3 and 4). It was proved that the molecular sizes of the recombinant proteins corresponded to dimeric and trimeric isoforms. An average expression of 1.03 g/L of E2his in days 2-8 subsequent to inoculation, with an average yield of 5.22 g for each animal was obtained. For the recombinant molecule E2his-CD154 was obtained an average expression of 0.73 g/L, with an average yield of 3.04 g per animal.

Example 5

Purification of E2his and E2his-CD154 Antigens from Goats' Milk

The samples from each milking day containing the E2his and E2his-CD154 recombinant vaccine antigens, respectively, were mixed and centrifuged at 15 000 g, during 30 min at 4° C. The soluble phase (milk serum) was separated and the fat phase was discarded. The collected serum was diluted in milk separating buffer (10 mM Tris-HCl, 10 mM $CaCl_2$, pH: 8.0) in a proportion 1:4. The mix was chilled on ice during 30 min and centrifuged at 15 000 g, during 30 min at 4° C. The supernatants and precipitates were analyzed by SDS-PAGE and Western blotting assay. It was determined that a major percent of such recombinant proteins were presents on the soluble phase but the precipitate contained caseins.

Serum fractions containing the recombinant antigens of interest (E2his and E2his-CD154) were clarified by sequential filtrations in membranes of 0.8 μM and 0.4 μM (Millipore) and were further applied in XK16 purification column (Amersham, USA) packed with an Ni-NTA-Agarose matrix (Qiagen, USA). Two washing steps with 100 mM phosphate buffer, 20 mM imidazole, pH 7.2 (first washing) and 100 mM phosphate, 50 mM imidazole, pH 7.2 (second washing) were performed. After washing, the protein of interest was eluted in 100 mM phosphate buffer, 200 mM imidazole, pH 7.2. The peak corresponding to the pure fraction was dialyzed against 10 mm phosphate buffer, pH 7.2 (FIG. 5).

The purification procedure of E2his and the E2his-CD154 from goat milk was the same for both vaccine antigens. The two proteins were obtained with a purity level higher to 90%. E2his was obtained with a recovering of 70% and in the case of E2his-CD154 a recovery of 58% was obtained. Purified proteins were analyzed by SDS-PAGE and Western blotting assay, in order to determine the protein aggregates formation. It could be determined that the dimeric isoforms (homodimers) of E2his produced on milk was recognized efficiently by the polyclonal serum from CSFV infected pigs, which indicates that this specific conformation increase the molecule antigenicity (FIG. 6).

Example 6

Construction of Expression Vectors in the *Pichia pastoris* Methylotrophic Yeast The pPS10 *P. pastoris* expression vector was digested with Nae I restriction endonuclease in order to incorporate the interest coding sequences in the 3' end of the secretion signal for *Saccharomyces cerevisiae* invertase sucrose (Suc2). The E2 coding sequence amplified by PCR was inserted on the Nae I restriction site of pPS10 plasmid. The E2his-CD154 coding sequence was removed from pMOS-E2his-CD154 plasmid by enzymatic digestion with Sma I-EcoR V restriction endonuclease and was inserted on the Nae I restriction site of pPS10. Thus, the pPS-E2his and pPS-E2his-CD154 plasmids were obtained. The coding sequences for both molecules were coupled to the secretion signal of Suc2 from *S. cerevisiae* and it remained under the transcriptional control of the *P. pastoris* yeast alcohol oxidase enzyme (AOX1) promoter.

The recombinant plasmids were linearized with the Pvu II restriction endonuclease and they were electroporated in electrocompetent cells of *P. pastoris* MP36 strain. Thus, several clones of *P. pastoris* MP36 strain stably transformed with the plasmids pPS-E2his and pPS-E2his-CD154 were generated. This strain is an auxotrophic mutant for histidine, therefore the recombinant yeast acquire a $His^+$ phenotype, allowing its auxotrophic selection.

The recombinant yeast, initially identified by Dot blotting assay, were also analyzed by Southern blotting assay in order to determine the integration pattern that can occur through the replacement of *P. pastoris* AOX1 gene, generating a $Mut^S$-His phenotype (low usage of methanol). The genic replacement of AOX1 occurs by recombination between the 5'AOX1 promoter region and 3' AOX1 region present in the yeast's genome and the other one present in the plasmid, driving to the elimination of the AOX1 gene coding region. Recombinant yeast with $Mut^S$ phenotype support the production of alcohol oxidase enzyme on the AOX2 gene but its growing rate in methanol is low. Also, a phenotype $Mut^+$-His integration pattern can be obtained by replacement.

The coding sequences for E2his and E2his-CD154 variants remained under the AOX1 promoter regulation control, which is inducible by methanol. *P. pastoris* secretes low levels of proteins and its culture media does not need supplementary proteins, therefore it can be expected that the secreted heterologous protein constitute the majority of the total proteins in the medium (until more than 80%). Recombinant protein production was carry out in fermentors of 5L. The induction of the expression was performed by the addition of methanol to the culture during 5 days and the recombinant proteins were obtained in the fermentation culture medium. The E2his was secreted to the recombinant yeast culture medium at levels of 0.143 mg/mL. In case of E2his-CD154, 0.122 mg/mL expression levels were obtained.

Example 7

Purification of E2his and E2his-CD154 Antigens from the *Pichia pastoris* Culture Medium The fermentation product was centrifuged at 10 000 g during 30 minutes, at 4° C. in order to separate the biomass from the liquid phase. The culture medium was filtrated on 0.8 μM and 0.2 μM membranes (Millipore) and it was applied in XK16 purification column (Amersham, USA) packed with a Ni-NTA Agarose matrix (Qiagen, USA). A washing with 100 mM phosphate buffer, 30 mM imidazole, pH 7.2 was performed and the interest protein was eluted with 100 mM phosphate buffer, 200 mM imidazole, pH 7.2. The pure fraction was dialyzed against phosphate buffer 10 mM. The procedure for the purification of E2his and E2-CD154 from the supernatant of fermentation of genetically transformed *P. pastoris* yeast, was identical for both vaccine antigens. The two proteins were obtained with a purity level higher to 95%. E2his was obtained with a recovery of 83% and in the case of E2his-CD154 it was obtained with a recovery of 78%.

Example 8

Protection Trial in Pigs Vaccinated with the Secretable E2his Variant

Twenty four healthy pigs, weighting about 20 kg, with negative serology to CSFV and belonging to a non-vaccinated and CSF free herd were used in this assay. The pigs were distributed in groups of 8 animals each and they were housed in three separate experimental rooms (A, B and C) with water and food ad libitum.

The animals from group A and group B were immunized with a vaccine formulation containing E2his antigen, in a single dose of 30 µg (group A) and 50 µg (group B) per animal, and group C was immunized with placebo. The antigen was formulated in a water-in oil emulsion and was inoculated by a 2 mL injection, by intramuscular route, in the neck. The placebo constituted by adjuvant and phosphate saline solution in a proportion 1:1 (V/V) was inoculated in the same conditions. In the third week post-immunization all animals were challenged with $10^5DL_{50}$ with homologous CSFV "Margarita" strain by intramuscular injection.

Figure 7:
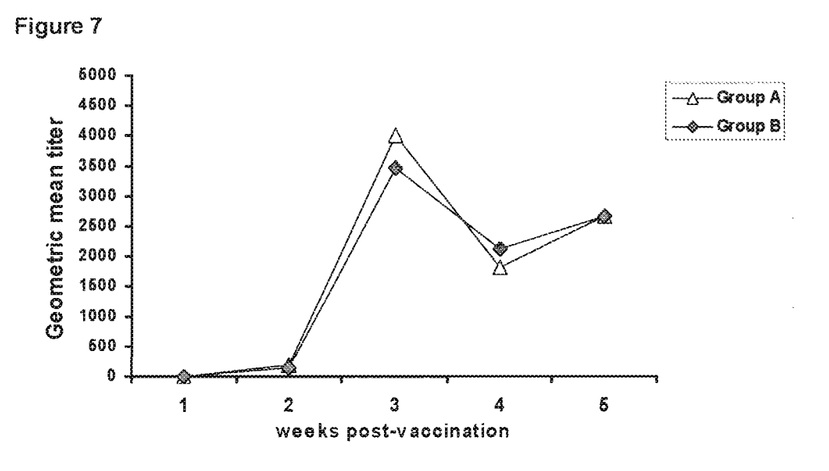
FIG. 7. Kinetics of neutralizing antibodies obtained in two groups of pigs vaccinated with a single dose of the E2his vaccine antigen, the antibodytiters were determined by a neutralizing peroxidase-linked assay. Group A was inoculated with a dose of 30 µg/animal and group B with a dose of 50 µg/animal. Both groups were challenged three weeks after the vaccination with a CSF viral dose of $10^5 DL_{50}$. The results are shown as the geometric mean of the reciprocal titers.

The inoculation with the E2his vaccine formulation did not produce adverse reactions, in view of the fact that no alterations of the normal clinic parameters were observed. Titers of neutralizing antibodies higher to 1/50 (considered protective) were obtained in the vaccinated groups following the second week of immunization. After the third week the titers increased until 1/1600-1/6400 (FIG. 7) but no differences in the immune response were observed between the vaccinated groups (A and B). The vaccinated pigs did not developed pyrexia or clinic symptoms of the disease and no viral isolates were made from the lymphocytes in the days subsequent to the challenge. However, the placebo group developed all clinical symptoms of the disease including pyrexia, hemorrhage and non-purulent encephalitis. In this group virus isolations were obtained from the fourth day post-challenge and until the sacrifice day. Here, it was demonstrated that weaning pigs vaccinated with E2his formulation, administered at a dose of 30 µg, with the vaccination scheme proposed, remained protected from clinical symptoms and CSFV infection.

Example 9

Vertical Protection Trial in Pregnant Sows Vaccinated with the Secretable E2his Antigen Ten sows serologically negative to CSFV, from a herd without CSF disease or vaccination history (3 years before) were taken. After weaning the estrous cycle was induced by hormonal treatment and three days later all sows were inseminated. The insemination was carried out simultaneously to the immunization. A group of 5 sows was taken and 2 mL of the vaccine formulation, mentioned in Example 7 (Group B), was applied in the neck by intramuscular injection. The remaining 5 sows were taken as a negative control group and were injected with a placebo, constituted by 2 mL of adjuvant and saline solution in a proportion 1:1 (V/V). The vaccinated group received a booster 21 days later. The pregnant sows were studied by measuring of the clinical triad (temperature, cardiac pulse and respiratory rate) and weekly blood extraction for hematology and detection of neutralizing antibodies against CSFV were carried out. Two months later the pregnant sows were challenge with $10^5$ $DL_{50}$ of homologous CSFV "Margarita" strain by intramuscular injection. Virus isolation from peripheral blood lymphocytes at days 3 and 5 post-challenge was performed in order to detect the presence of CSFV. Two weeks post-challenge the sows were sacrificed and the fetus were removed for morphologic and anatomy-pathological analysis and virus isolation assay. During the experiment the sows had access to water and food ad libitum.

The vaccine resulted innocuous for all pregnant sows and there were no abortion or clinical alterations in the days post-immunization. The vaccinated animals developed specific neutralizing antibodies against CSFV with titers between 1:50 to 1:51200. The sows from the vaccinated group remained completely healthy after challenge. None of these animals presented pyrexia, leucopenia, thrombocytosis or any other CSF clinical sign.

An analysis by morphometry and pathological anatomy allow determining that fetuses from vaccinated sows have a normal size and did not present histopathological lesions. The CSFV was not isolated from leucocytes neither the dam's blood samples in extractions subsequent to the challenge nor in blood or in the sacrificed fetuses organs.

Sows from the placebo group had pyrexia and leucopenia after the challenge. One of the sows had an abortion in the day 8 post-challenge and was sacrificed in the day 9 post-challenge. Pathological signs like little size, mummification, splenomegaly, several petechiae in kidneys and urinary bladder and non purulent encephalitis were observed in the fetuses from sows sacrificed at 2 week post challenge and in the aborted fetuses. CSFV was isolated in the blood and all organs from fetuses of this group. Vaccination of pigs with the E2his vaccine formulation prevented the CSFV transmission from sows to the offspring.

Example 10

Early Protection Trial in Vaccinated Pigs with the E2his-CD154 Vaccine Formulation Four groups of 6 pigs each were taken (in the same conditions as in example 8) and the vaccine formulation was applied with the following amounts of antigen: 50 µg of E2his-CD154 (Group D), 80 µg of E2his-CD154 (Group E), 50 µg of E2his (Group F). Group G was taken as a placebo. Antigens were formulated in a "water in oil" emulsion and 2 mL were inoculated by IM injection, the placebo group was inoculated with adjuvant without proteins. The vaccines were applied in a single dose. The animals were challenged, on day $8^{th}$ post-immunization, through IM inoculation with $10^5DL_{50}$ CSFV "Margarita" strain. Clinical signs were recorded daily during the experiment period and a weekly blood extraction for the hematological analysis and neutralizing antibodies was carried out. Also, blood samples in days 1, 3, 5 and 7, subsequent to the vaccination were taken to evaluate the cellular immunological response by lymphoproliferation and "antiviral activity in serum" assays.

Figure 8:
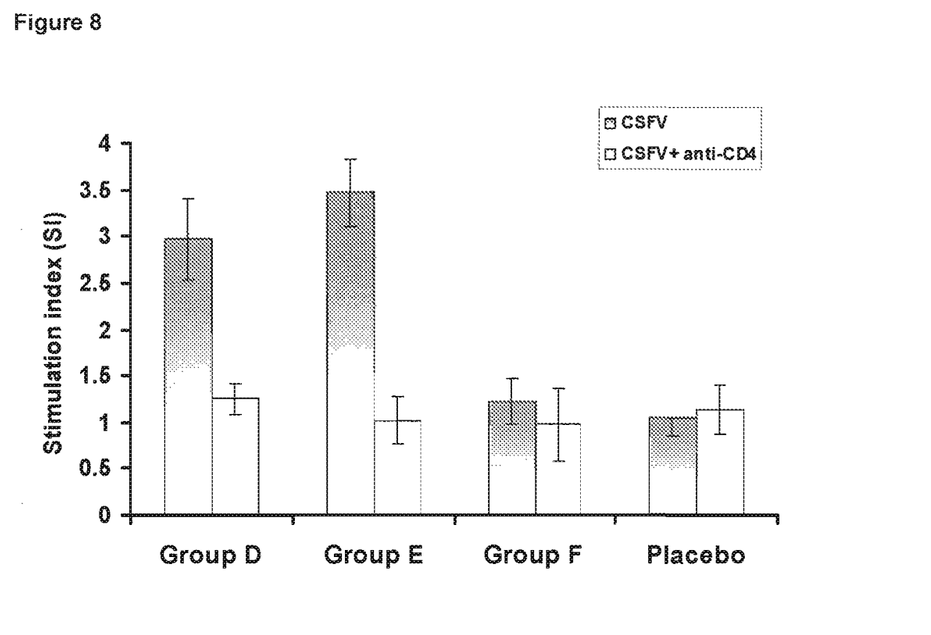
FIG. 8. Lymphoproliferative assay using the lymphocytes isolated from pigs in the day 5 subsequent to the vaccination with E2-CD154 antigens (groups D and E) and E2his (group F). Results are expressed as the stimulation index (SI), defined as the ratio between the values of count per minute (cpm) of the stimulated culture and the values of cpm of the untreated control culture. The lymphoproliferative response that induced an SI≧2 was considered as positive. It was evaluated the proliferation in the cultures treated with CSFV, as well as the inhibition of the proliferation in cultures treated with CSFV and a Mab against the swine CD4 domain.

After vaccination, normal clinical signs and non adverse reactions at inoculation site were observed. Increased lymphocyte counting was detected on the lymphocyte cultures from animals vaccinated with E2-CD154 antigen (Groups D and E) and phytohemagglutinin mitogen at the lymphoproliferation assay. This response was blocked with a Mab against the CD4 domain, which indicates that the immune response was mediated by T helper lymphocytes. During the assay lymphocyte samples of the animals from groups F and G (placebo) did not respond to stimulation neither with mitogen nor with CSFV (FIG. 8).

Figure 9:
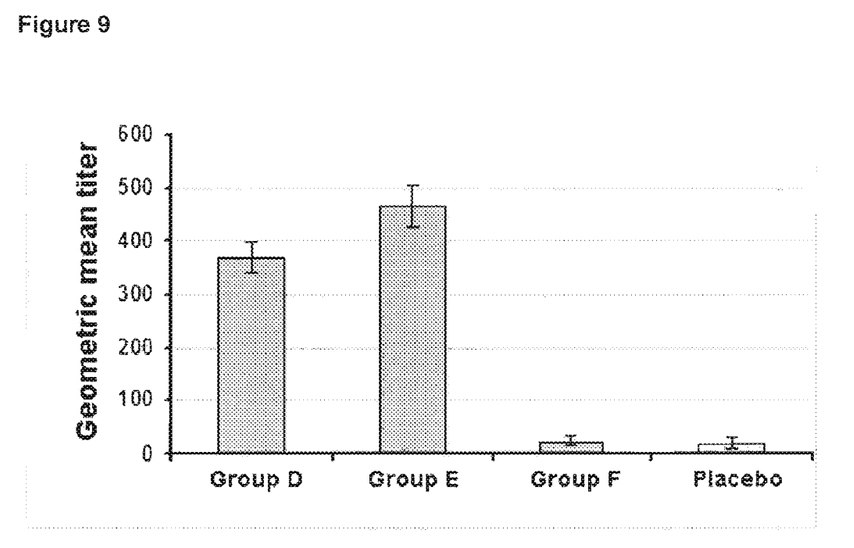
FIG. 9. Antiviral activity assay in PK-15 cells, using the serum from pigs vaccinated with E2-CD154 (Groups D and E) and E2his (Group F) antigens. The results are expressed as the geometric mean reciprocal of the titers.

High interferon alpha titers were observed in samples on days 3, 5 and 7 subsequent to vaccination with E2-CD154 antigen on groups D and E. However, interferon was not detected in animals vaccinated with E2his antigen (Group F) and the placebo group (G) during the experimental time. An "antiviral activity assay" against transmissible gastroenteritis virus was performed on PK-15 cells. In groups D and E antivirus activity titers of 1:512 were obtained; nevertheless, antiviral protection was not detected in samples from E2his immunized pigs neither on the placebo group (FIG. 9). With these experiments it was determined that the E2 antigen coupled to CD154 molecule enhances the cellular immune response against CSFV which is related with the CD154 immunostimulant activity.

Example 11

Comparison of the Neutralizing Antibodies Kinetics in Pigs Vaccinated with a Single Dose of Vaccine Formulations Containing E2his and E2his-CD154

Three groups of 6 pigs, of approximately 20 kg of weight, serologically negative to CSFV, from a herd without CSF disease or vaccination history (3 years before) were taken. The animals were supplied with water and daily food ad libitum.

Each animal was vaccinated with 50 μg of E2his-CD154 on Group H; 50 μg of E2his on Group I and the Group J was taken as a placebo. Antigens were formulated in a "water in oil" emulsion and 2 mL were inoculated by IM injection, the placebo group was inoculated with adjuvant without proteins. A single dose was applied and the levels of neutralizing antibodies were measured by a neutralization peroxide linked assay (NPLA) during 5 weeks post-immunization.

Figure 10:
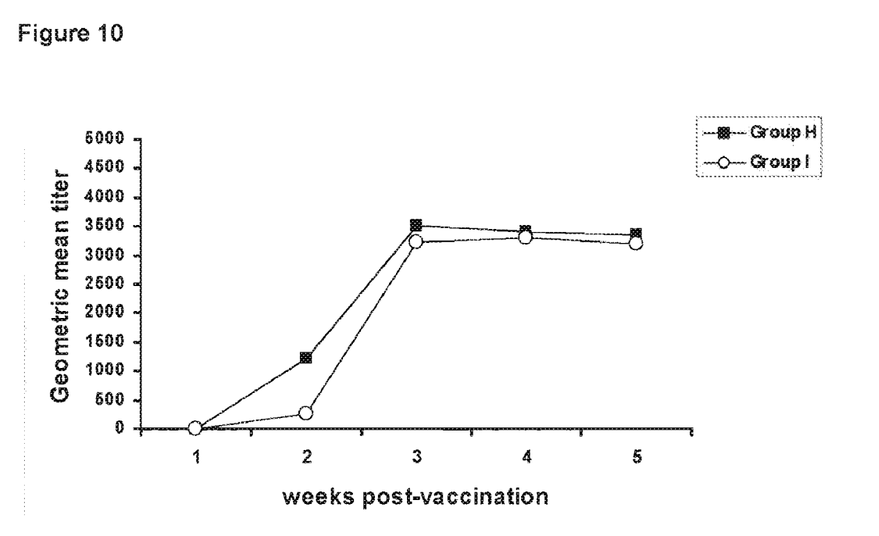
FIG. 10. Kinetics of neutralizing antibodies obtained in two groups of pigs vaccinated with E2-CD154 (Group H) and E2his (group I) antigens, using a dose of 50 µg/animal. The antibodies titers were determined by a neutralizing peroxidase-linked assay. The results are shown as the geometric mean of the reciprocal titers.

Neutralizing antibodies were detected since the second week of immunization, with titers above 1:50 (considered protective), in the groups vaccinated with E2-CD154 and E2 his (H and I). No antibodies were detected in animals from placebo group during the trial. The neutralizing antibody titers of animals from group H (E2-CD154 antigen) were higher than those from the group immunized with the E2his antigen at the second week post-immunization. Those results suggested a higher stimulation of the humoral response in animals of Group H (FIG. 10).

We concluded that the E2his-CD154 vaccine formulation in a dose level of 50 μg is safe, immunogenic and induces an early humoral response in vaccinated pigs when it is compared with the E2his vaccine formulation.

Example 12

Vertical Protection Trial in Pregnant Sows Vaccinated with E2his-CD154 Vaccine Formulation Ten sows were selected with the same health conditions and origin of those used in example 8. After weaning the estrous cycle was induced by hormonal treatment and three days later all sows were inseminated. Simultaneously, a group of 5 sows was immunized with 2 mL of E2his-CD154 vaccine formulation (80 μg/animal; composition used on example 10 for group E), by IM injection behind the ear, on the neck. The group of 5 pigs remaining was immunized with adjuvant as placebo. The pregnant sows were studied by measuring the clinical triad (temperature, cardiac pulse and respiratory rate) and weekly blood extractions for hematology and detection of neutralizing antibodies against CSFV were carried out. At 2 month of pregnancy the animals were challenged with $10^5$ $DL_{50}$ of CSFV "Margarita" strain. The viremia was tested from blood extracted on days 3 and 5 post-challenge. Two weeks later, sows were sacrificed and the fetuses were removed for a virological, morphological and pathological analysis. During the experiment sows had access to water and daily food ad libitum.

Non abortion cases or another CSF clinical signs were observed after the immunization. Thus, the E2his-CD154 vaccine formulation in a single immunization resulted safe in pregnant sows. Vaccinated animals developed specific neutralizing antibodies titers against CSFV from 1:50 to 1:16 000.

After challenge, it was not observed pyrexia, leucopenia, or thrombocytosis in the group of vaccinated sows. In this group the fetuses had a normal size and no histophatological lesions, determined by morphometry and pathologic anatomy analysis were found. CSFV was not found on the leucocytes from the blood samples taken after the challenge from vaccinated dams, neither in organs nor blood of their fetuses.

Sows from the placebo group had pyrexia, leucopenia and anorexia after challenge. Fetuses from this group had a reduced size and showed histopathological lesions compatible with CSF, as splenomegaly, petechiae in kidneys and urinary bladder, necropsys on intestine; several hemorrhage in the internal organs and non purulent encephalitis. CSFV was isolated from all organs and blood of the fetuses from this group. Vaccination of pregnant sows with the E2his-CD154 vaccine formulation, applied in the evaluated schedule, prevented CSFV transmission form sows to the offspring.

The invention claimed is:

1. A vaccine composition against Classical Swine Fever virus (CSFV), said vaccine comprising a chimeric protein comprising a) only the extracellular segment of E2 glycoprotein of virus envelope of CSFV and b) only the extracellular segment of CD154 molecule.

2. The composition according to claim 1, wherein the extracellular segment of CD 154 molecule is from a mammal.

3. The composition according to claim 2, wherein the amino acid sequence of the extracellular segment of E2 glycoprotein from CSFV is identified as SEQ ID NO: 1 and the extracellular segment of the CD 154 molecule is identified as SEQ ID NO: 2.

4. The composition according to claim 1, wherein said chimeric protein is generated from milk of genetically modified mammals.

5. The composition according to claim 4, wherein said chimeric protein is generated through direct genetic transformation of the mammary gland.

6. The composition according to claim 5, wherein the direct genetic transformation of the mammary gland is carried out by employing adenovirus vectors.

7. The composition according to claim 1, wherein said chimeric protein is generated from milk of transgenic mammals.

8. The composition according to claim 1, wherein said composition is suitable for administering to animals by systemic or mucosal route.

* * * * *

UNITED STATES PATENT AND TRADEMARK OFFICE
CERTIFICATE OF CORRECTION

PATENT NO. : 8,409,562 B2
APPLICATION NO. : 12/280055
DATED : April 2, 2013
INVENTOR(S) : Toledo Alonso et al.

It is certified that error appears in the above-identified patent and that said Letters Patent is hereby corrected as shown below:

IN THE SPECIFICATION:

Column 4, line 21

Now reads: "based on naked desoxirribonucleic acid";

Should read: -- based on naked deoxyribonucleic acid --.

Signed and Sealed this
Fifth Day of November, 2013

Teresa Stanek Rea
*Deputy Director of the United States Patent and Trademark Office*

SEQUENCE LISTING

<160> NUMBER OF SEQ ID NOS: 2

<210> SEQ ID NO 1
<211> LENGTH: 363
<212> TYPE: PRT
<213> ORGANISM: Classical Swine Fever Virus
<220> FEATURE:
<221> NAME/KEY: PEPTIDE
<222> LOCATION: (1)..(363)
<223> OTHER INFORMATION: Polypeptide sequence of the 363 aa
      corresponding to the E2 CSFV extracellular segment

<400> SEQUENCE: 1

Lys Val Leu Arg Gly Gln Val Val Gln Gly Val Ile Trp Leu Leu
 1               5                  10                  15

Val Thr Gly Ala Gln Gly Arg Leu Ala Cys Lys Glu Asp Phe Arg Tyr
            20                  25                  30

Ala Ile Ser Ser Thr Asn Glu Ile Gly Leu Leu Gly Ala Glu Gly Leu
        35                  40                  45

```
Thr Thr Thr Trp Lys Asp Tyr Asp His Asn Leu Gln Leu Asp Asp Gly
 50                  55                  60
Thr Ile Lys Ala Ile Cys Thr Ala Gly Ser Phe Lys Val Ile Ala Leu
 65                  70                  75                  80
Asn Val Val Ser Arg Arg Tyr Leu Ala Ser Leu His Lys Gly Ala Leu
                 85                  90                  95
Pro Thr Ser Val Thr Phe Glu Leu Leu Phe Asp Gly Thr Ser Pro Ser
                100                 105                 110
Ile Glu Glu Met Gly Asp Asp Phe Gly Phe Gly Leu Cys Pro Phe Asp
                115                 120                 125
Thr Ser Pro Val Val Lys Gly Arg Tyr Asn Thr Thr Leu Leu Asn Gly
                130                 135                 140
Ser Ala Phe Tyr Leu Val Cys Pro Ile Gly Trp Thr Gly Val Ile Glu
145                 150                 155                 160
Cys Thr Ala Val Ser Pro Thr Thr Leu Arg Thr Glu Val Val Lys Thr
                165                 170                 175
Phe Arg Arg Glu Lys Pro Phe Pro His Arg Lys Asp Cys Val Thr Thr
                180                 185                 190
Thr Val Glu Asn Glu Asp Leu Phe Tyr Cys Arg Leu Gly Gly Asn Trp
                195                 200                 205
Thr Cys Val Lys Gly Glu Pro Val Ile Tyr Thr Gly Gly Leu Val Lys
                210                 215                 220
Gln Cys Arg Trp Cys Gly Phe Asp Phe Asn Glu Pro Asp Gly Leu Pro
225                 230                 235                 240
His Tyr Pro Ile Gly Lys Cys Ile Leu Ala Asn Glu Thr Gly Tyr Arg
                245                 250                 255
Ile Val Asp Ser Thr Asp Cys Asn Arg Asn Gly Val Val Ile Ser Thr
                260                 265                 270
Glu Gly Ser His Glu Cys Leu Ile Gly Asn Thr Ser Val Lys Val His
                275                 280                 285
Ala Leu Asp Glu Arg Leu Gly Pro Met Pro Cys Arg Pro Lys Glu Ile
                290                 295                 300
Val Ser Ser Glu Gly Pro Val Arg Lys Thr Ser Cys Thr Phe Asn Tyr
305                 310                 315                 320
Thr Lys Thr Leu Arg Asn Lys Tyr Tyr Glu Pro Arg Asp Ser Tyr Phe
                325                 330                 335
Gln Gln Tyr Met Leu Lys Gly Glu Tyr Gln Tyr Trp Phe Asp Leu Asp
                340                 345                 350
Val Thr Asp His His Ser Asp Tyr Phe Thr Glu
                355                 360

<210> SEQ ID NO 2
<211> LENGTH: 210
<212> TYPE: PRT
<213> ORGANISM: Sus scrofa
<220> FEATURE:
<221> NAME/KEY: PEPTIDE
<222> LOCATION: (1)..(210)
<223> OTHER INFORMATION: CD154 extracellular domain of 210 aa
      obtained taking as a sequence pattern the CD154
      gene of pig "Sus scrofa" (AB040443).

<400> SEQUENCE: 2

Lys Ile Glu Asp Glu Arg Asn Leu His Glu Asp Phe Val Phe Ile Lys
 1               5                  10                  15
Thr Ile Gln Arg Cys Lys Gln Gly Glu Gly Ser Leu Ser Leu Leu Asn
                 20                  25                  30
```

```
                    -continued
Cys Glu Glu Ile Arg Ser Gln Phe Glu Asp Leu Val Lys Gly Ile Met
         35                  40                  45

Gln Ser Lys Glu Val Lys Lys Glu Lys Ser Phe Glu Met His Lys
     50                  55                  60

Gly Asp Gln Asp Pro Gln Ile Ala Ala His Val Ile Ser Glu Ala Ser
 65                  70                  75                  80

Ser Lys Thr Ala Ser Val Leu Gln Trp Ala Pro Lys Gly Tyr Tyr Thr
             85                  90                  95

Leu Ser Thr Asn Leu Val Thr Leu Glu Asn Gly Arg Gln Leu Ala Val
            100                 105                 110

Lys Arg Gln Gly Ile Tyr Tyr Ile Tyr Ala Gln Val Thr Phe Cys Ser
        115                 120                 125

Asn Arg Asp Ala Ala Gly Gln Ala Pro Phe Ile Ala Ser Leu Cys Leu
    130                 135                 140

Arg Ser Pro Ser Gly Ser Glu Arg Ile Leu Leu Arg Ala Ala Asn Thr
145                 150                 155                 160

His Ser Ser Ser Lys Pro Cys Gly Gln Gln Ser Ile His Leu Gly Gly
                165                 170                 175

Val Phe Glu Leu Gln Pro Gly Ala Ser Val Phe Val Asn Val Thr Asp
            180                 185                 190

Pro Ser Gln Val Ser His Gly Thr Gly Phe Thr Ser Phe Gly Leu Leu
        195                 200                 205

Lys Leu
    210
```